(12) United States Patent
Lambert et al.

(10) Patent No.: US 6,424,850 B1
(45) Date of Patent: *Jul. 23, 2002

(54) NON-INVASIVE GLUCOSE MONITOR

(75) Inventors: James L. Lambert, Sunland; Mark S. Borchert, La Canada, both of CA (US)

(73) Assignees: Childrens Hospital Los Angeles, Los Angele; California Institute of Technology, Pasadena, both of CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 09/690,113

(22) Filed: Oct. 16, 2000

Related U.S. Application Data

(63) Continuation of application No. 09/351,788, filed on Jul. 12, 1999
(60) Provisional application No. 60/092,545, filed on Jul. 13, 1998.

(51) Int. Cl.[7] .................................................. A61B 5/00
(52) U.S. Cl. ..................................................... 600/319
(58) Field of Search ................................ 600/310, 316, 600/317, 318, 319

(56) References Cited

U.S. PATENT DOCUMENTS

| | | | |
|---|---|---|---|
| 5,243,983 A | 9/1993 | Tarr et al. | |
| 5,433,197 A | 7/1995 | Stark | |
| 5,535,743 A | * 7/1996 | Backhaus et al. | ........... 600/310 |
| 5,553,617 A | 9/1996 | Barkenhagen | |
| 5,666,956 A | 9/1997 | Buchert | |
| 5,710,630 A | 1/1998 | Essenpreis et al. | |

OTHER PUBLICATIONS

Erckens et al.; Raman Spectroscopy for Non–Invasive Characterization of Ocular Tissue: Potential for Detection of Biological Molecules, Abstract, *J. of Raman Spectroscopy*, 28(5):293–9 (May 1997).

Schulze HG et al.; Artificial Neural Network and Classical Least–Squares Methods for Neurotransmitter Mixture Analysis, Abstract, *J. Neurosci Methods*, 56(2):155–167 (Feb. 1995).

Berger, A.J. et al.; Feasibility of Measuring Blood Glucose Concentration by Near–Infrared Raman Spectroscopy, Abstract, *Spectrochim Acta A Mol Biomol Spectrosc*, 53A(2):287–292 (Feb. 1997).

Berger, A.J. et al.; Rapid, Noninvasive Concentration Measurements of Aqueous Biological Analytes by Near–Infrared Raman Spectroscopy, Abstract, *Applied Optics*, 35(1):209–12 (Jan. 1, 1996).

Wicksted et al., Raman Spectroscopy Studies of Metabolic Concentration in Aqueous Solutions and Aqueous Humor Specimens, *Applied Spectroscopy*, 49(7):987–993 (1995).

Wang et al.; Analysis of Metabolites in Aqueous Solutions by Using Laser Raman Spectroscopy, *Applied Optics*, 32(6):925–929 (Feb. 20, 1993).

* cited by examiner

*Primary Examiner*—Eric F. Winakur
(74) *Attorney, Agent, or Firm*—Myers Bigel Sibley & Sajovec (57) ABSTRACT

A non-invasive method for determining blood level of an analyte of interst, such as glucose, comprises: generating an excitation laser beam (e.g., at a wavelength of 700 to 900 nanometers); focusing the excitation laser beam into the anterior chamber of an eye of the subject so that aqueous humor in the anterior chamber is illuminated; detecting (preferably confocally detecting) a Raman spectrum from the illuminated aqueous humor; and then determining the blood glucose level (or the level of another analyte of interest) for the subject from the Raman spectrum. Preferably, the detecting step is followed by the step of subtracting a confounding fluorescence spectrum from the Raman spectrum to produce a difference spectrum; and determining the blood level of the analyte of interest for the subject from that difference spectrum, preferably using linear or nonlinear multivariate analysis such as partial least squares analysis. Apparatus for carrying out the foregoing method is also disclosed.

11 Claims, 8 Drawing Sheets

NON-INVASIVE GLUCOSE MONITOR

This application is a continuation of commonly owned, copending application Ser. No. 09/351,788, filed Jul. 12, 1999, the disclosure of which is incorporated by reference herein in its entirety.

This application claims the benefit of U.S. Provisional Application No. 60/092,545, filed Jul. 13, 1998, the disclosure of which is incorporated by reference herein in its entirety.

FIELD OF THE INVENTION

The present invention concerns methods and apparatus for the non-invasive monitoring of blood glucose levels by spectrographic analysis of the aqueous humor in the anterior chamber of the eye.

BACKGROUND OF THE INVENTION

Non-invasive measurement of blood glucose by any method including optical spectroscopy techniques has remained an elusive target for at least two decades. Blood, tissue, and most excreted fluids contain numerous substances which confound glucose spectral signatures. On the other hand, aqueous humor (AH) filling the anterior chamber of the eye (between the lens and cornea) contains relatively few molecules capable of interfering with the spectroscopic detection of glucose. These are primarily lactate, ascorbate, and urea. This fact, and its optically accessible location behind the cornea, make AH an attractive choice as a site on which to attempt non-invasive analysis of glucose.

Pohjola (*Acta Ophthalmologica Suppl.* 88, 1–80 (1996)) showed that the ratio of aqueous glucose to plasma glucose in normal euglycemic individuals is related to age and ranges from 0.6 to 0.9. He further showed in seven humans with steady-state hyperglycemia that similar ratios applied. No data exists on the equilibration time of aqueous humor glucose with changes in plasma glucose in humans.

Numerous investigators over the years have suggested that the ratio of aqueous glucose to plasma glucose in the normoglycemic rabbit ranges from 0.42 to 1.01 (S. Pohjola, supra; D. Reddy and V. Kinsey, *Arch. Ophthalmol.* 63, 715–720 (1960); M. Reim et al., *Ophthalmologica* 154, 39–50 (1967); W. March et al., *Diabetes Care* 5, 259 (1982)). It is uncertain whether this variability is normal or could be attributed to differences in glucose measurement techniques, collection techniques, sample storage, and anesthesia. The relationship of aqueous glucose to rising, or falling, plasma glucose has not been previously studied in rabbits.

Coté has reviewed the relative strengths and weaknesses of optical glucose sensing techniques (*J. Clin. Engineering* 22, 253 (1997)). Raman spectroscopy is potentially attractive because it can distinguish glucose in water solutions containing various levels of other optically active metabolites (S. Wang et al., *Applied Optics* 32, 925 (1993)). Raman spectroscopy measures the shift in the wavelength of incident light as it is scattered by molecules. Any given molecule causes a characteristic shift in the spectrum of scattered light, which is dependent upon its intermolecular and intramolecular bonds. This is in contradistinction to fluorescence, which is caused by changes in electron energy states, and does not shift relative to the wavelength of incident light.

Wicksted et al, (*Appl. Sectroscop.* 49, 987 (1995)) suggest that the Raman signature for glucose can be identified in aqueous humor samples, and Goetz, et al (*IEEE Trans. Biomed. Eng.* 42, 728 (1995)), have demonstrated that higher than physiologic levels of glucose can be measured with Raman spectroscopy in water solutions. J. Lambert et al., (*LEOS Newsletter* 12, 19–22 (1998)) suggest that measurement of glucose at physiologic levels is possible in water solutions containing other analytes normally found in aqueous humor. When solutions containing fluorescent substances are studied, however, the fluorescence signal can overwhelm the relatively weak Raman-shifted signal. This is a potential problem if Raman spectroscopy is applied to aqueous humor, which contains proteins that fluoresce.

U.S. Pat. No. 5,243,983 to Tarr et al. suggest a non-invasive blood glucose measurement system using stimulated Raman spectroscopy. Stimulated Raman spectroscopy requires the use of both a pump and a probe laser beam. The probe laser beam is used to measure the stimulated Raman light at a single wavelength after transmission across the anterior chamber of the eye. This is undesirable, since an optical component contacting the eye is required to direct the beam across the anterior chamber. In addition, use of a single wavelength may limit the ability to measure glucose at physiologic levels within tissue containing many other Raman scattering chemicals.

U.S. Pat. No. 5,433,197 to Stark suggests a non-invasive glucose measurement apparatus that employs broad band infrared light stimulation.

U.S. Pat. No. 5,553,617 to Barkenhagen suggests a non-invasive method for measuring body chemistry from the eye of a subject by measuring a spectral response such as a Raman scattering response. While it is suggested that the invention may be used for medical applications such as the determination of sugar in diabetics, specific details on how this might be accurately carried out are not provided.

U.S. Pat. No. 5,710,30 to Essenpreis suggests a method for measuring the concentration of glucose in a biological sample such as the eye (see FIG. 4 therein) with interferometric measurement procedures.

U.S. Pat. No. 5,666,956 to Buchert et al. suggests that an instrument for the non-invasive measurement of a body analyte can be based on naturally emitted infrared radiation.

In spite of the foregoing efforts, a commercially viable, non-invasive, blood glucose monitor based on a non-invasive analysis of the aqueous humor of the eye has not yet been developed. Difficulties in developing such a device include correlation of aqueous humor glucose levels to blood glucose levels, the difficulty of obtaining accurate measurements, and the need to minimize damaging effects to the eye caused by excessive exposure to light in an instrument that will be used by subjects on a repeated basis. Accordingly, there is a continued need for new methods for the non-invasive analysis of blood glucose levels.

SUMMARY OF THE INVENTION

A first aspect of the present invention is a non-invasive method for determining blood level of an analyte of interst, such as glucose. The method comprises:

generating an excitation laser beam (e.g., at a wavelength of 700 to 900 nanometers);

focusing the excitation laser beam into the anterior chamber of an eye of the subject so that aqueous humor in the anterior chamber is illuminated;

detecting (preferably confocally detecting) a Raman spectrum from the illuminated aqueous humor; and then determining the blood glucose level (or the level of another analyte of interest) for the subject from the Raman spectrum. Preferably, the detecting step is followed by the step of subtracting a confounding fluorescence spectrum from the Raman spectrum to produce a difference spectrum; and determining the blood level of the analyte of interest for the subject from that difference spectrum, preferably using linear or nonlinear multivariate analysis such as partial least squares or artificial neural network algorithms.

A second aspect of the present invention is an apparatus for the non-invasive determination of the blood level of an analyte of interest such as glucose in a subject. The apparatus comprises:

- a laser for generating an excitation laser beam (e.g., at a wavelength of from 700 to 900 nanometers);
- an optical system (e.g., a confocal optical system) operatively associated with said laser for focusing the excitation laser beam into the anterior chamber of an eye of the subject so that aqueous humor in the anterior chamber is illuminated;
- a detector operatively associated with the optical system and configured to detect a Raman spectrum from the illuminated aqueous humor;
- preferably a subtraction system, hardware and/or software processor or other suitable means for subtracting a fluorescence spectrum for said aqueous humor from said Raman spectrum to produce a difference spectrum; and
- a processor for determining the blood level of the analyte of interest for said subject from the Raman spectrum (or preferably the difference spectrum). Numerous additional features may be incorporated into the apparatus. The apparatus may include an visual display screen for visually displaying the results of the test to the subject through the same aperture as which the test is conducted. It may include a visual fixation device, also visible through the test aperture, which controls movement of the eye and simultaneously insures that focusing of the laser beam is properly directed into the anterior chamber of the eye. The processor may contain an empirical model of actual testing experience to determine the blood level of the analyte of interest. The apparatus may employ a tunable laser, a plurality of fixed wavelength lasers, or other means for sliding the Raman spectrum passed a plurality of different wavelength detectors to obviate the need for a full grating based Raman spectrometer. A communication line connected to the processor for transmitting the blood level of the analyte of interest to a remote location.

Still other features that can be included in the methods and apparatus described above set forth below.

BRIEF DESCRIPTION OF THE DRAWINGS

FIG. 7b schematically illustrates an apparatus of the invention that utilizes the method illustrated in FIG. 7a.

DETAILED DESCRIPTION OF THE PREFERRED EMBODIMENTS

The term "glucose" as used herein preferably refers to D-glucose.

The term "subject" as used herein refers to both human subjects and animal subjects such as dogs, cats, and rabbits. Animal subjects may be used in the present invention for veterinary purposes. Human subjects are preferred.

The term "processor" as used herein refers to a hardware device, a software or program-implemented device running on a general-purpose computer, or combinations of such hardware and software devices.

The present invention is primarily concerned with the determination of blood glucose levels, and is so explained herein. However, the blood concentration of other Raman-active molecules or analytes such as lactate, urea, ascorbate, drugs, steroids, and alcohol (particularly ethanol) may also be determined by these techniques.

The step of generating an excitation laser beam pulse can be carried out with any suitable laser beam source. The power of the excitation laser beam pulse should be sufficiently low to avoid tissue toxicity, but sufficiently high to provide a measurable Raman signal from the aqueous humor. In general, the laser beam pulse will be at a wavelength of from 700 to 900 nanometers, and more preferably will be at a wavelength of 780 to 860 nanometers to reduce fluorescence, increase tissue penetration, and reduce phototoxicity to the eye. The duration of the pulse will typically be from 1 to 2 seconds to 30 seconds or 60 seconds (i.e., one-half minute to one minute). The total energy of the laser pulse will typically be 200–500 milliJoules with instantaneous power not exceeding 30 or 50 milliwatts. The optical components of the apparatus used to carry out the method are preferably configured so that energy on the retina of the eye (as well as other areas susceptible to tissue toxicity, such as the lens and cornea) from the excitation laser beam pulse is not greater than 3000 milliwatts per square centimeter, and more preferably not greater than 2000, 1000 or even 500 milliwatts per square centimeter.

Any source laser that provides. the desired frequency output may be employed in carrying out the invention. A distributed feedback laser can be used to reduce instrument size. Tunable or multiple fixed frequency lasers can be combined with bandpass filters (Puppels et al., *Applied Spectroscopy* 47, 1256–67 (1993)) that select for Raman scattering at wavelengths that provide optimum information for multivariate analysis (this reduces the cost and size of the instrument compared to the use of holographic filters or gratings).

Any suitable detector can be used to detect a Raman spectrum from illuminated aqueous humor. A CCD detector or CCD camera is preferred. The CCD detector preferably has high quantum efficiency in the near infrared range. The high quantum efficiency may be achieved by any suitable means, such as employing a backthinned detector, but one sufficiently thick to reduce etalon effect.

The fluorescence spectrum for the aqueous humor can be subtracted from the Raman spectrum by stimulating the aqueous humor with a second excitation laser light pulse at a wavelength slightly different from that of the first pulse (e.g., up to two nanometers from the first pulse), and then subtracting one spectrum from the other in a processor in accordance with conventional techniques. Such techniques are known. See, e.g., Funfschilling and Williams, *Applied Spectroscopy* 30, 443 (1976); Baraga et al., *Applied Spectroscopy* 46, 187 (1992); Wicksted et al., *Applied Spectroscopy* 49, 987 (1995)). In the alternative, the fluorescence spectrum can be subtracted out through the use of software or other processing techniques. Thus the term "subtraction" as used herein is intended to include techniques such as filtering. While not essential, other potentially interfering spectra or signals such as Raman scattering from the lens, iris, or cornea, can also be filtered or subtracted through a hardware and/or software processor. Water is typically not an issue for Raman spectroscopy, but a water spectrum can be subtracted if desired.

The blood glucose level for the subject is then determined from the difference spectrum by an empirically based model, formula, or matrix of actual subject or sample testing in a hardware and/or software processor. The model can be obtained through linear (e.g., partial least squares) or non-linear (e.g.,artificial neural networks) multivariate analysis. It is important that the training set of Raman spectra used for the multivariate analysis include samples from aqueous humor with a broad range of concentrations of the Raman scattering metabolites. The principal Raman-scattering metabolites (or "Raman active compounds") (glucose, lactate, urea, ascorbate, and any exogenous compounds or drugs present) preferably should not vary co-linearly with one another among the samples in the training set. The model can be produced with spectra samples obtained from one or more prior subjects, can be produced with spectra samples obtained from the subject from whom the current blood level of the analyte of interest is being determined (in which case that subject would be required to provide a blood sample for determination of the blood concentration of the analyte of interest), or both. Typically, the training set would require at least 20, 25 or 30 Raman spectra samples (and samples of the corresponding blood levels of the analyte of interest) with substantial inter-sample variability in the levels of the major Raman scattering metabolites (e.g., glucose, ascorbate, lactate, urea, and any drugs or exogenous compounds present). The concentration of the analyte of interest (in either the blood or aqueous humor) should vary by at least a factor of 2, 5, 10 or 20 or more from the sample with the lowest concentration to the sample with the highest concentration. This may require development of the model using subjects with multiple different diseases (e.g., renal failure, diabetes, seizures, mitochondrial myopathies, sickle cell disease, heart failure, blood clots, etc.). For human appplications, the model may even be determined with spectra samples obtained from animals, particularly primates. The aqueous humor sample may be a natural sample, (human or animal), or may be a man-made or surrogate aqueous humor sample created to mimic natural samples, where the blood level is calculated from a priori knowledge of the relationship between blood levels and aqueous humor levels for the analyte of interest.

Figure 5:
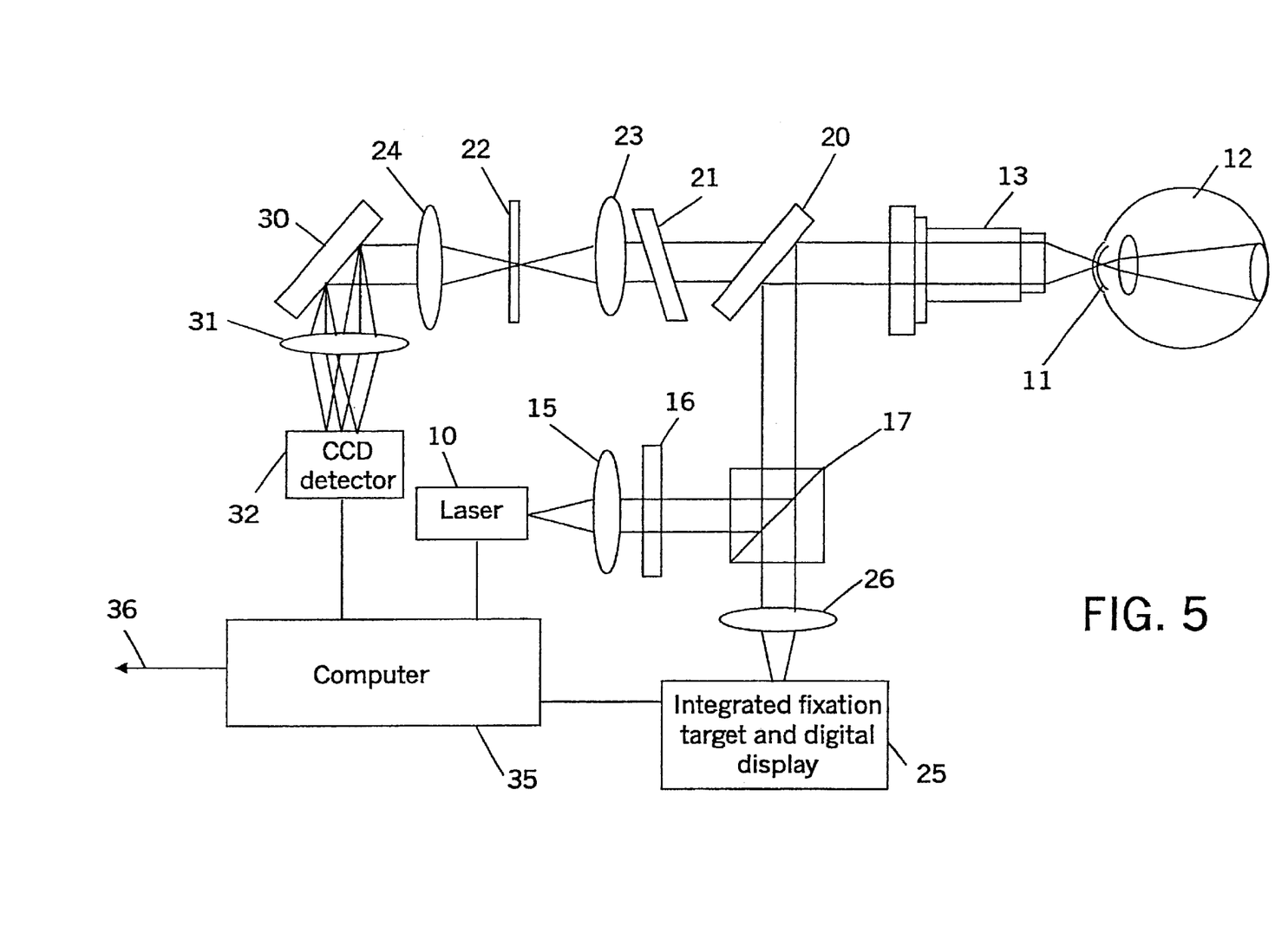
FIG. 5 schematically illustrates a first embodiment of an apparatus of the invention.

For example, where the analyte of interest is glucose, the training set of samples for the empirical model should comprise at least 20, 25 or 30 aqueous humor spectra samples, with the corresponding blood glucose levels, where the principal Raman active compounds in the aqueous humor samples (glucose, ascorbate, lactate, urea, and preferably any exogenous compounds such as drugs) vary substantially non-colinearly among the samples, with either the blood or aqueous humor glucose concentration ranging from 0 or 50 mg/dL to 800 or 1,000 mg/dL, and with there being at least 100, 200, 300 or 400 mg/dL difference in said concentration between the sample with the lowest concentration and the sample with the highest A schematic diagram of the general apparatus is depicted in FIG. 5. A tunable, narrow-band laser beam from laser 10 is focused into the anterior chamber 11 of the eye 12 through an objective or ocular lens 13 via lens 15 and filter 16, beam splitter 17, and filter 20. A non-fluorescing objective lens is chosen with suitable numerical aperture (e.g. 0.2–0.5) such that Raman scattering from the aqueous humor is maximized while scattering from adjacent structures (e.g. lens, cornea, and iris) is minimized. The objective lens should have adequate working distance to permit focusing of the laser into the middle of the anterior chamber of the eye without touching the cornea. An integrated fixation target projected from display screen 25 is projected via lens 26 through the same objective lens as the laser, but is focused on the retina of the eye. Focusing this fixation target on the retina simultaneously controls direction and focusing of the laser light in the anterior chamber.

The light collected by the objective lens is directed through holographic notch filters 20, 21 to remove the Raleigh scattered light. The Raman scattered light passes through these filters with minimal attenuation and is focused through a confocal pinhole aperture 22 by lenses 23, 24. The pinhole and the focal point in the anterior chamber of the eye are confocal such that light from adjacent structures in the eye is filtered at this aperture. The pinhole also serves as the entrance aperture to the spectrometer. The spectrometer shown is an imaging spectrograph with a grating 30, lens 31 and a CCD detector array 32. A computer 35 controls the laser 10, the fixation target and readout display 25, and receives data from the CCD detector 32. The architecture of the spectrometer is merely an example of one that is suitable for this application. Many types of spectrographs could be utilized including Fourier transform spectrographs, spectrographs using liquid crystal tunable filters or other tunable elements. Information can be transmitted to a remote source such as a computer, database, remote physician or the like via modem or other connection through a suitable communication line 36 via the internet, world wide web, etc.

The CCD detector in the spectrograph is of a red-shifted, back-thinned, thick epitaxial design such that its sensitivity is optimal in the 700–1100 nanometer spectral region. Other types of very sensitive detectors may be suitable as well.

As noted above, a digital computer processes the output of the CCD detector and controls the frequency and the power of the laser source. The computer switches the frequency of the laser to permit subtraction of fluorescence as described previously. The computer also provides information to a digital display imaged onto the retina. The patient reads the results of the analysis on this display.

Figure 6:
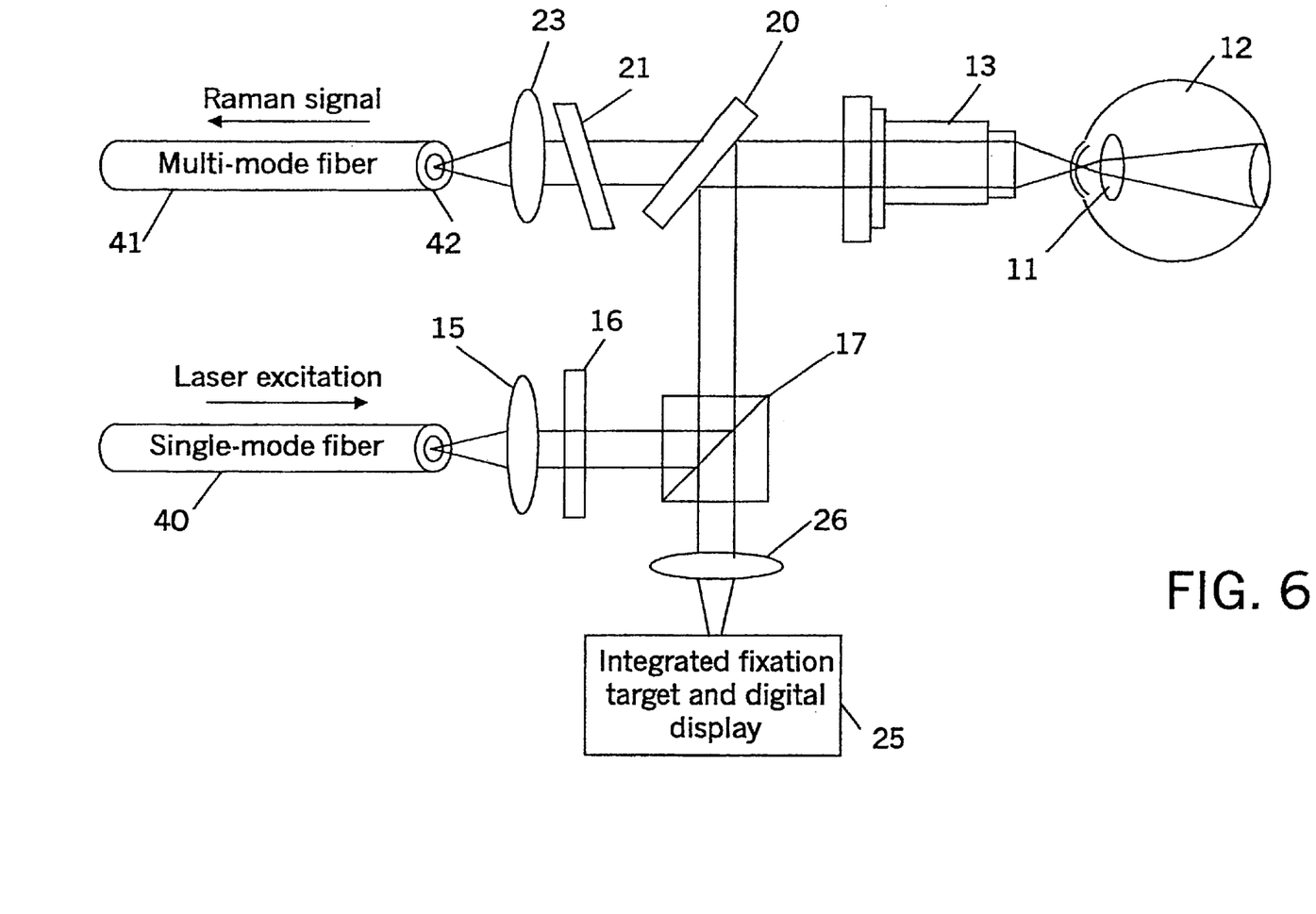
FIG. 6 schematically illustrates a second embodiment of an apparatus of the invention.

Fibers 40, 41 may be used to deliver the laser beam and collect the Raman scattered light as depicted in FIG. 6. (like components in FIGS. 5 and 6 are assigned the same numbers). In this embodiment the confocal aperture is a circular aperture 42 placed on the end of a multimode fiber. As with the pinhole aperture in FIG. 5, the end of said fiber is placed so that it is confocal with the objective lens' focal point in the anterior chamber of the eye. A single mode fiber is used to deliver the laser beam into the anterior chamber. This single mode fiber insures a diffraction limited spot size at the focal point of the objective.

Figure 7A:
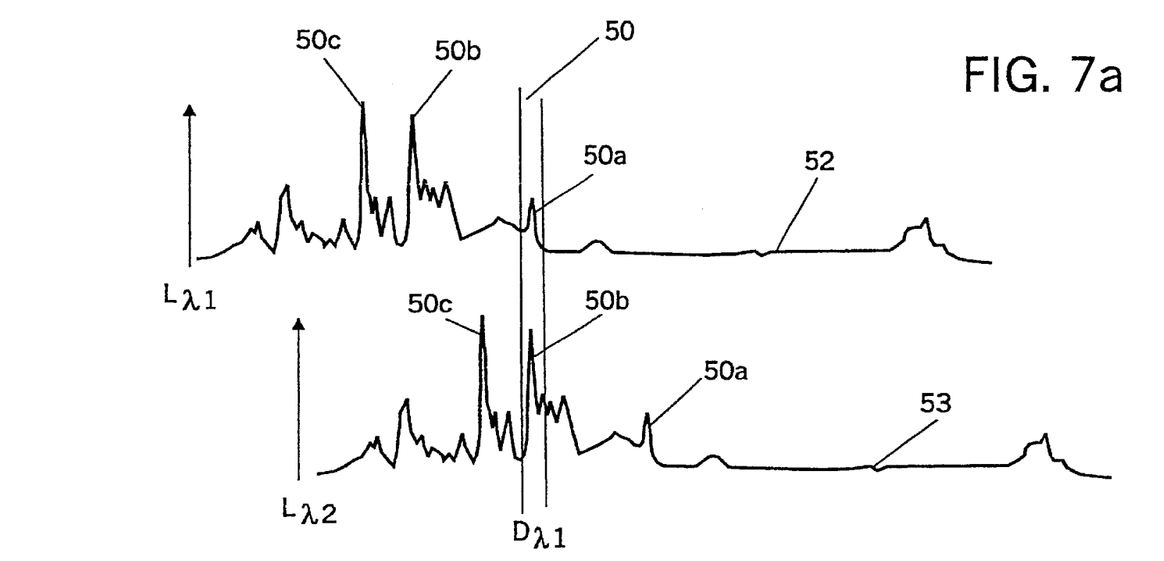
FIG. 7a schematically illustrates the method of sliding Raman spectra features through a particular detector window by changing excitation frequency.
Figure 7B:
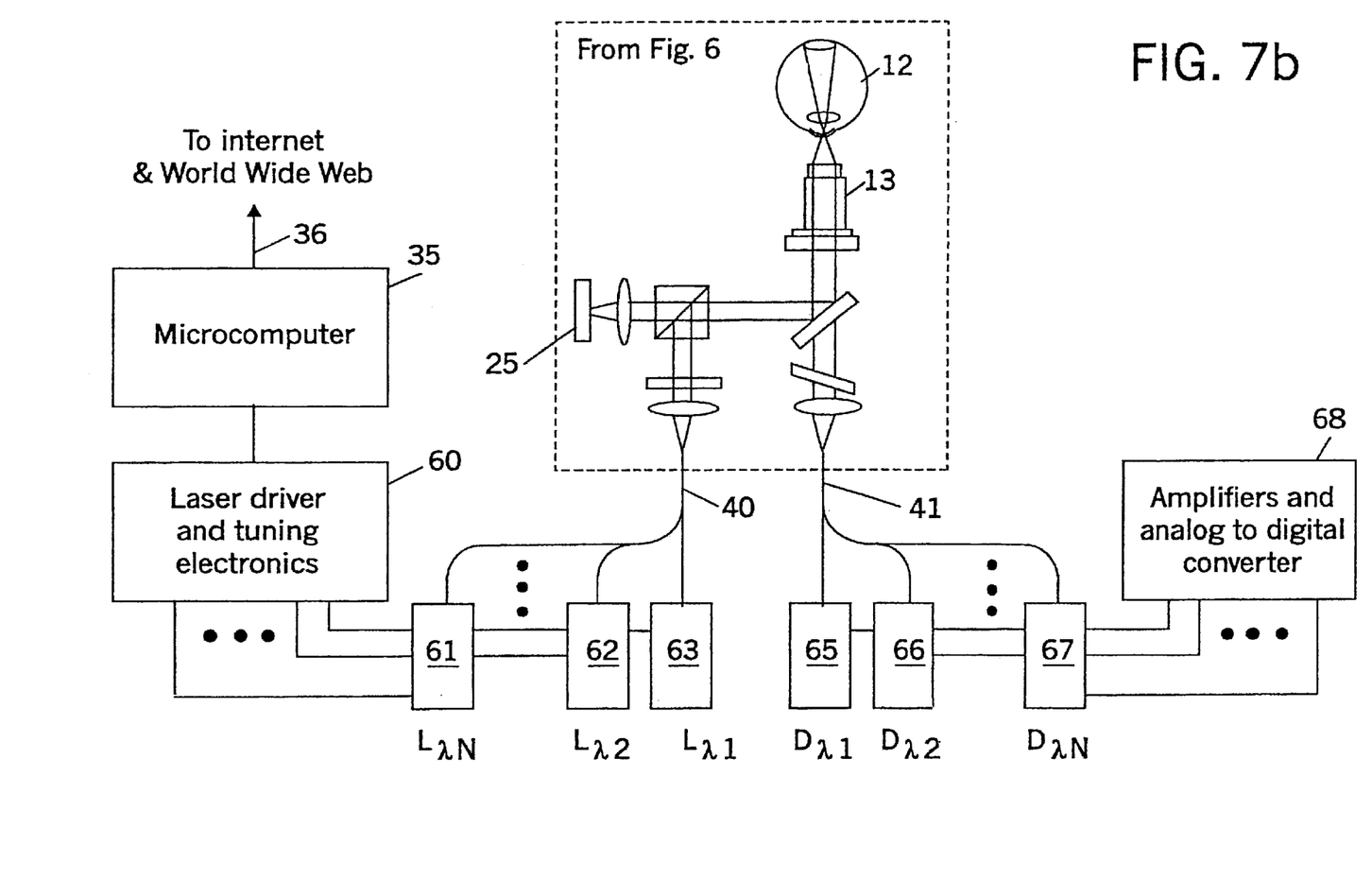

Such a fiber delivery and collection system depicted in FIG. 6 can be connected to an alternative detection system shown in FIGS. 7a–b. This alternative detection system will allow for subtraction of the fluorescence spectrum and as well as selected sampling of the frequencies most important for calculation of glucose concentration. Such an alternative detection system would decrease the size and cost of the instrument.

The system depicted in FIG. 7 uses one or more fixed frequency or tunable lasers to illuminate the aqueous humor of the eye using the optical delivery system shown in FIG. 6.

FIG. 7a illustrates that each spectral feature 50a, 50b, 50c of the Raman scattered light is related to the excitation wavelength by a fixed offset, usually expressed in wavenumbers. Changing the excitation wavelength causes the Raman spectra to shift in wavelength, as depicted by the different feature captured in detector range $D_{\lambda 2}$ 51 based on Raman spectra 52 for excitation frequency $L_{\lambda 1}$ as compared to Raman spectra 53 for excitation frequency $L_{\lambda 2}$.

An apparatus that takes advantage of the foregoing is schematically illustrated in FIG. 7b. Like components to FIGS. 5 and 6 are assigned like numbers. Laser Drivers and or tuning electronics 60 are operatively associated with a tunable laser or a plurality of fixed wavelength lasers 61, 62, 63. A series of one or more bandpass filter/detector elements 65, 66, 67 operatively associated with amplifiers and analog to digital converter 60 is used to sample the spectrum of the collected light. The center wavelength and bandwidth of each filter is chosen to correspond with a different Raman spectral peak of aqueous humor important for quantification of glucose. If this laser is tunable over a nanometer or so, subtraction of the fluorescent components of the acquired spectrum would also be possible as discussed earlier. Using a laser with a wider tuning range would allow the Raman shifted spectra to be scanned or slid across a smaller number of bandpass filter/detectors. Since semiconductor lasers with extremely wide tuning ranges are not readily available, one could instead use a set of narrowly tunable lasers each with a different center wavelength as the laser means in conjunction with a series of bandpass filter/detectors for this purpose.

Advantageously, the systems described herein may be configured so that optical components need not and do not contact the cornea of the eye during use, which many patients find objectionable (e.g., by providing a suitable monocular eye cup for contacting the orbit around the eye).

The apparatus of the invention can be implemented as a spectrometer base unit attached by a fiberoptic cable to an ocular probe, or as a single integrated unit including foreoptics, spectrometer, detector, computer and display.

Figure 8:
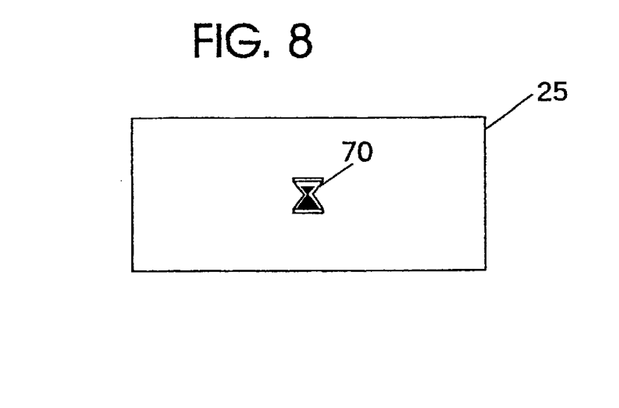
FIG. 8 illustrates a visual fixation display that can be utilized in an apparatus of the invention.
Figure 9:
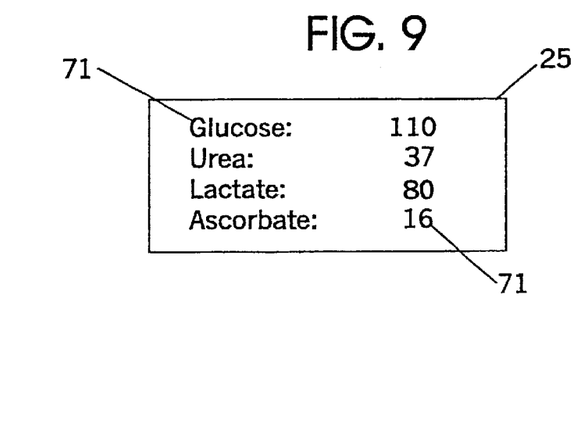
FIG. 9 illustrates a visible readout display that can be utilized in an apparatus of the invention.

As noted above, a visual fixation target such as a mirror, LED or the like can be built into the optical apparatus to facilitate focusing of the excitation light into the anterior chamber and maintain stability of the eye. In the embodiment of FIGS. 5–7, a display screen such as a liquid crystal display is employed. As shown in FIG. 8, a blinking fixation target in the form of an hourglass 70 can be displayed, focused on the retina, during acquisition of the spectra by the apparatus. This will help optimize the Raman signal from the aqueous humor and reduce light exposure to other structures of the eye. The fixation target is active and displayed during the time that the laser beam is active and illuminating the subject's aqueous humor. As shown in FIG. 9, a visible indication of the results of the test in the form of alphanumeric indicia 71 (or other suitable form, such as a graphical display) can be displayed on the same screen immediately after the acquisition step. The indicia of FIG. 9 provide a readout for all of the principal Raman-active compounds of the aqueous humor, but only one need be so displayed.

The instrument of the invention can be operatively associated with a patient's insulin pump (for D-glucose) or to a dialysis machine (for urea) by electrical or fiber optic lines, radio frequency transmitters and receivers or the like to provide information on the appropriate analyte that can then be used to control that apparatus and increase or decrease the output of the insulin pump in response to blood glucose levels, or to regulate the dialysis machine.

In telemedicine applications, the instrument of the invention can be conveniently operatively associated with a remote read-out terminal through a computer, modem, internet connection or other communication line with any any suitable means (such as an electrical or fiber optic lines, radio frequency transmitters and receivers, etc.) to provide information on the blood analyte to a remote physician or medical provider (e.g., through the internet or world wide web).

The present invention is explained in greater detail in the following non-limiting Examples, in which "$\mu L$" means microliters; "dL" means deciliters, "mW" means milliwatts, "nm" means nanometers, "Kg" means kilograms, "J" means Joules, "$cm^2$" means square centimeters, and temperatures are given in degrees Centigrade.

EXAMPLE 1

Measurement of Aqueous Humor Glucose in vitro with Raman Spectroscopy

Aqueous humor was obtained from sixteen New Zealand white rabbits within one minute of sacrifice by other investigators. These animals had experienced experimental myocardial infarction 48 hours prior to euthanasia. They were sacrificed by rapid exsanguination under ketamine and xylazine anesthesia. Aqueous humor samples were kept frozen until glucose levels could be measured and Raman spectroscopy performed. Glucose concentration was measured with a commercial glucometer (Glucometer Elite, Bayer, Elkhart, Ind., USA) and confirmed against concentration standards. Each measurement was repeated, and the average measurement was considered actual glucose concentration.

Samples were placed in conical quartz cuvettes designed to hold a volume of 80 μL and permit direct optical access to the solution by the spectrometer without traversing glass walls or coverslips.

Raman spectroscopy was performed with a f/1.8 holographic imaging spectrograph (Kaiser Optical Systems, Ann Arbor, Mich., USA) attached to an Olympus BX60 microscope with 10× objective. Data were collected using a Princeton Instruments (Trenton, N.J., USA) camera with a 1024×256 CCD array (EEV, United Kingdom) cooled to −80° C. with liquid nitrogen. Illumination of the sample through the microscope objective was achieved with a Ti:Sapphire laser (Spectra Physics 3900S, Mountain View, Calif., USA) pumped by an argon laser (Spectra Physics 2010E). Spectrographic data was integrated while the sample was illuminated at a wavelength of 785.0 nm (30 mW) for 10 seconds. This was then repeated at a wavelength of 787.2 nm.

Figure 1:
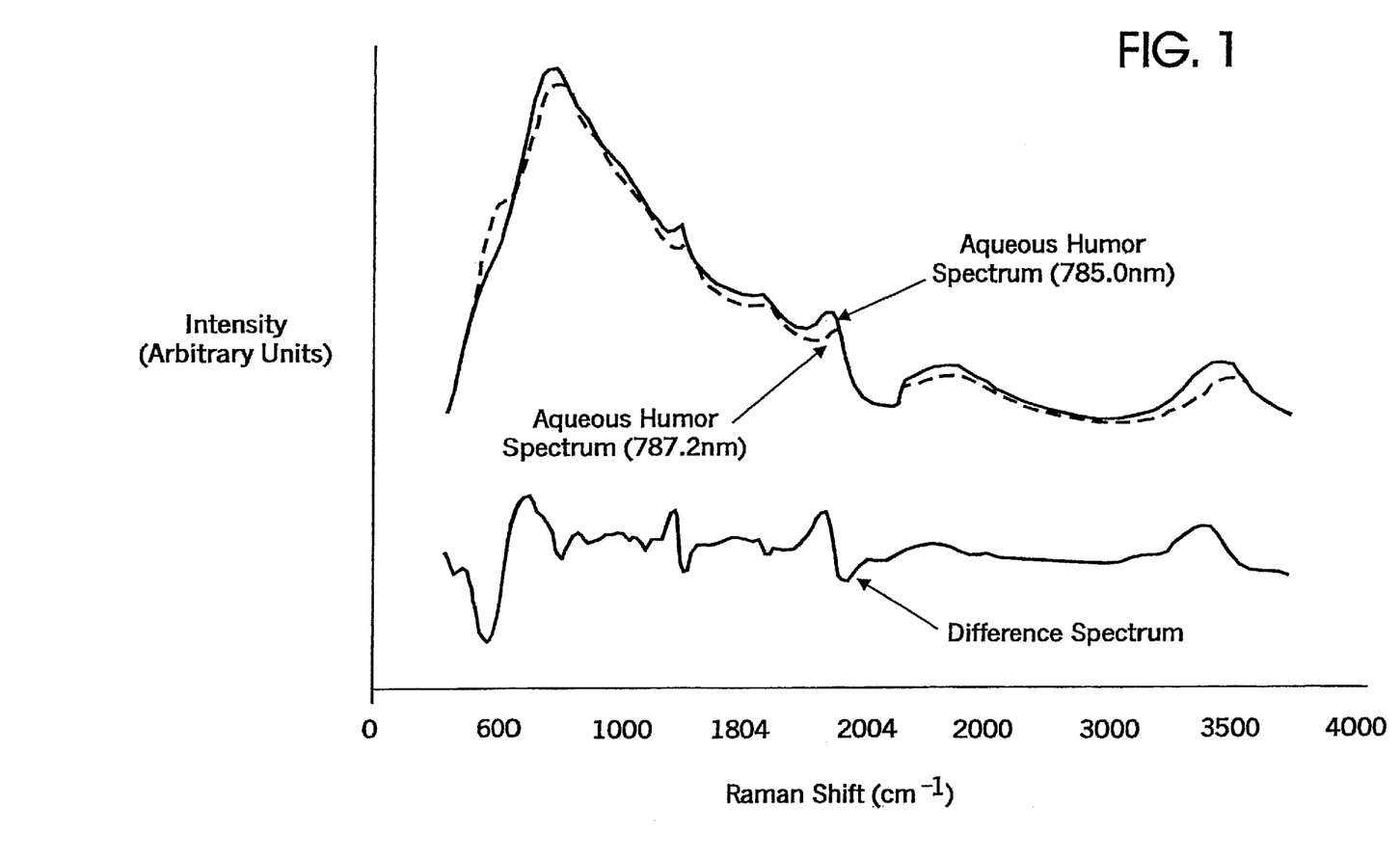
FIG. 1 illustrates that the broad fluorescence spectrum of aqueous humor can obscure the underlying peaks of interest in the Raman spectrum. Unlike the fluorescence spectrum, the Raman spectra will shift with a change in the excitation wavelength. The raw spectrum of rabbit aqueous humor is shown takien at 2 slightly different wavelengths (top). The difference spectrum (bottom) achieved by subtracting 1 raw spectrum from the other reveals a resultant bipolar Raman signature. Linear and nonlinear multivariate analysis can then be applied.

The integrated spectra at the two slightly different wavelengths were then subtracted from one another. This effectively eliminates the broadband fluorescence, which does not shift relative to the excitation wavelength. It leaves the Raman-shifted spectra appearing as a bipolar pattern. (FIG. 1)

Multivariate analysis of the spectra was accomplished using Holograms (Princeton Instruments, Trenton, N.J.) and Grams (Galactic Industries, Salem, N.H. USA) software packages. Thirty-two aqueous humor samples (from sixteen rabbits) were evaluated using a "round robin" approach to iteratively group all but one of the samples into a training set. Hence, the system trains on all but one of the samples, estimates the glucose level in that sample, then rotates the test sample into the training set. This cycle is repeated until all samples have served as an unknown test sample.

We subsequently employed a backpropagation neural network (D. Rumelhart et al., *Nature* 323, 533 (1986)) to determine if a nonlinear regression method would better predict the glucose concentration from the Raman spectra of aqueous humor. Such a model may compensate for as yet unknown interactions between analytes in aqueous humor. We employed a two-layer backpropagation neural network (NeuralWare, Inc., Pittsburgh, Pa., USA) using a sigmoidal function as the nonlinear element. Factors derived from the partial least squares algorithm served as the inputs to the neural network. Raw spectral data could have been used but would have required a prohibitively large training set. As in the linear regression preformed earlier, round robin training and testing was utilized. During training, the neural network's weights were adjusted to minimize the total squared error between the actual glucose concentration and the predicted glucose concentrations. Each sample was tested using a neural network trained on the remaining 31 samples.

EXAMPLE 2

Correlation of Aqueous Humor Glucose with Rising Blood Glucose

Nine female New Zealand white rabbits were used for this part of the study. They were anesthetized with ketamine (50 mg/kg) and xylazine (7.5 mg/kg) given as a single intramuscular injection. Xylazine blocks release of insulin from the pancreas and causes blood glucose to rise (K. Chalabi et al., *Ophthalmic Res.* 19, 289 (1987); J. Arnbjerg et al., *Ophthalmic Res.* 22, 265 (1990)).

Blood samples were taken from the central ear arteries at various times following the injection of anesthetic once the animals were adequately anesthetized. Whole blood was immediately measured for glucose concentration with a commercial glucometer (Glucometer Elite, Bayer). In most instances two measurements were made. The average measurements are reported. If the measurements differed by more than 20%, a third measurement was made. If one measurement differed by more than 20% from the mean, it was discarded. In instances when blood glucose concentration appeared stable, occasionally only one measurement was made.

At various times after induction of anesthesia, samples of aqueous humor were taken. This was done by paracentesis with a 25-gauge needle through clear cornea near the limbus after administration of proparacaine eye drops. Aqueous humor glucose concentration was measured with the glucometer in a manner similar to the blood.

In rabbits, there is massive breakdown of the blood-aqueous barrier after a single paracentesis of the anterior chamber of the eye (W. Unger et al., *Exp. Eye Res.* 20, 255 (1975)). The aqueous humor becomes too viscous for repeat paracentesis for at least 30 minutes. Consequently, our results are reported for the first paracentesis of an eye. In a few instances, however, a second paracentesis was made an hour later to assess how the breakdown of the blood-aqueous barrier may have affected the correlation of aqueous glucose with plasma glucose.

Average blood glucose concentrations for each animal were plotted against time after anesthetic injection. Since it was impossible to obtain blood samples simultaneous with aqueous humor samples, a best-fit second-order polynomial was calculated for each animal. This was used to calculate the blood glucose concentration at the time that the aqueous humor sample was taken. Aqueous humor glucose concentration was then plotted against the calculated simultaneous blood glucose concentration for all animals. DeltaGraph software (Delta Point, Inc., Monterey, Calif. USA) was used for all statistical calculations.

EXAMPLE 3

Results for Measurement of Aqueous Humor Glucose in vitro with Raman Spectroscopy The raw spectra of rabbit aqueous humor show broad fluorescence peaks that obscure the underlying Raman signature. (FIG. 1) When the spectra from the two slightly different wavelengths are subtracted, one from the other, the Raman shifted spectra become apparent as bipolar peaks.

Figure 2:
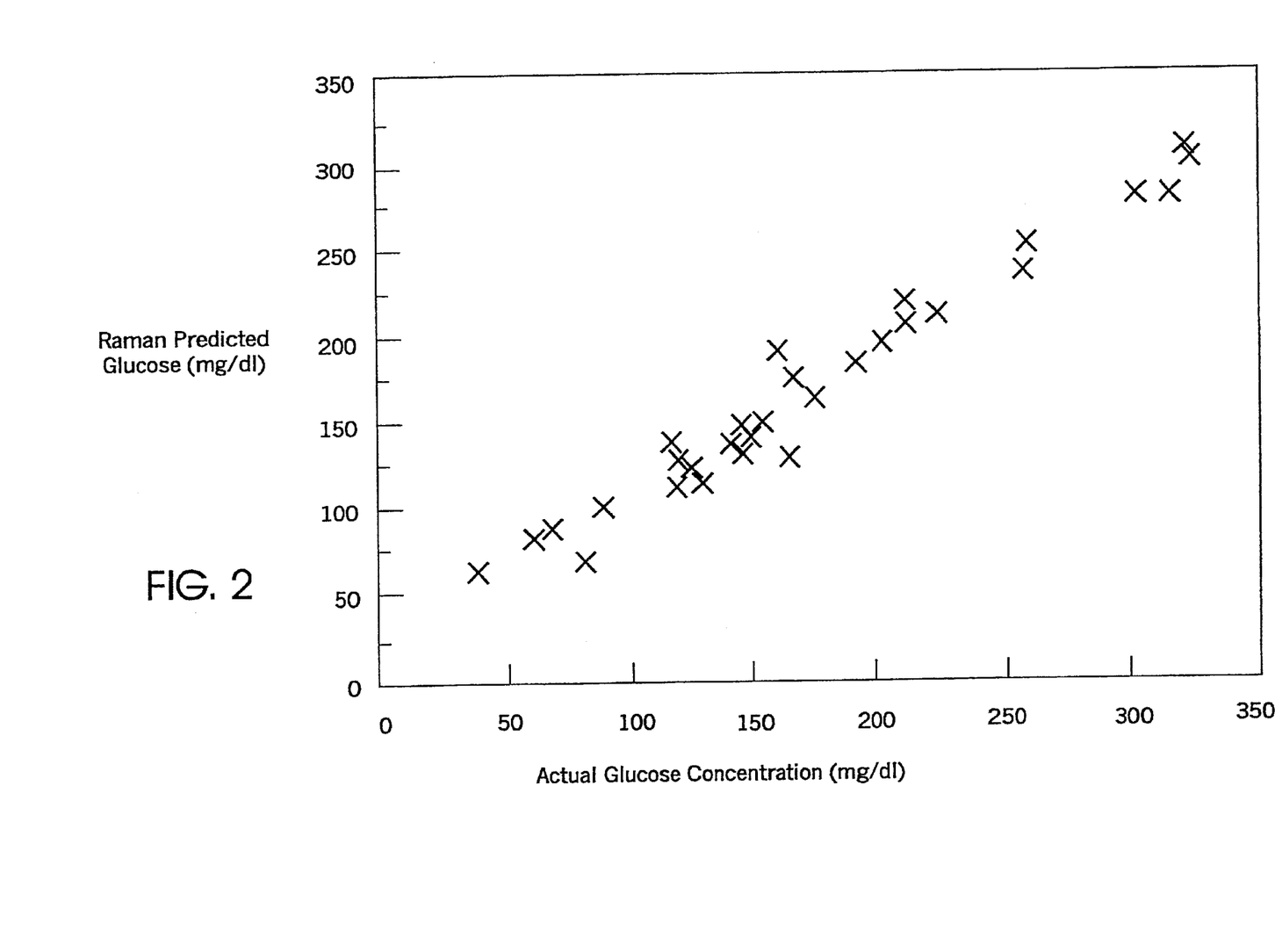
FIG. 2. The glucose concentration in aqueous humor from 16 rabbits was estimated with Raman spectroscopy and compared to the actual glucose concentration measured with a commercial glucometer. The graph shows the Raman predicted glucose concentration after subtracting fluorescence, and applying a linear partial least square algorithm followed by nonlinear backpropagation with an artificial neural network. This resulted in a high degree of correlation ($r^2=0.98$) of predicted with actual glucose concentration. Applying the partial least squares algorithm alone resulted in lesser correlation ($r^2=0.90$).

Actual aqueous humor glucose concentration, measured by the glucometer, ranged from 37 to 323 mg/dL in the thirty-two samples. Multivariate analysis of the raw spectra from these samples with the partial least squares algorithm revealed fair correlation ($r^2$=0.76) between the predicted aqueous humor glucose concentration and the actual concentration. Multivariate analysis of the subtracted spectra from these samples with the partial least squares algorithm resulted in improved correlation ($r^2$=0.90) between the predicted aqueous humor glucose concentration and the actual concentration. When backpropagation with an artificial neural network is further applied to the data, correlation is excellent ($r^2$=0.98). (FIG. 2).

EXAMPLE 4

Results for Correlation of Aqueous Humor Glucose with Rising Blood Glucose

Figure 3:
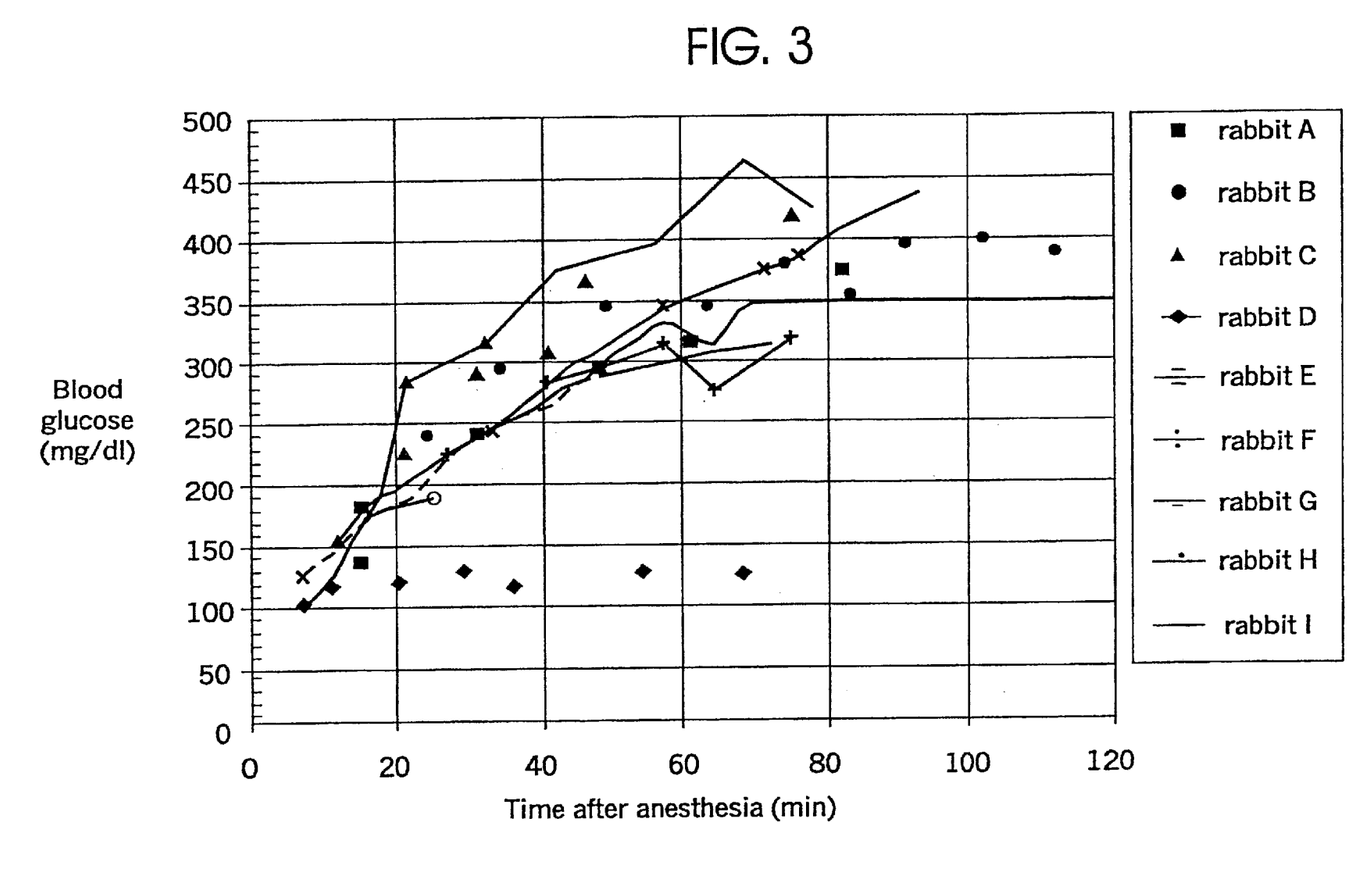
FIG. 3. Blood glucose steadily rises at variable rates in rabbits after administration of xylazine anesthesia. On animal (rabbit D, filled diamonds) had little change in blood glucose for unknown reasons.

The rate of rise of blood glucose after xylazine injection is highly variable from animal to animal. (FIG. 3) In fact, in one rabbit there was little change in the blood glucose concentration over time.

Figure 4:
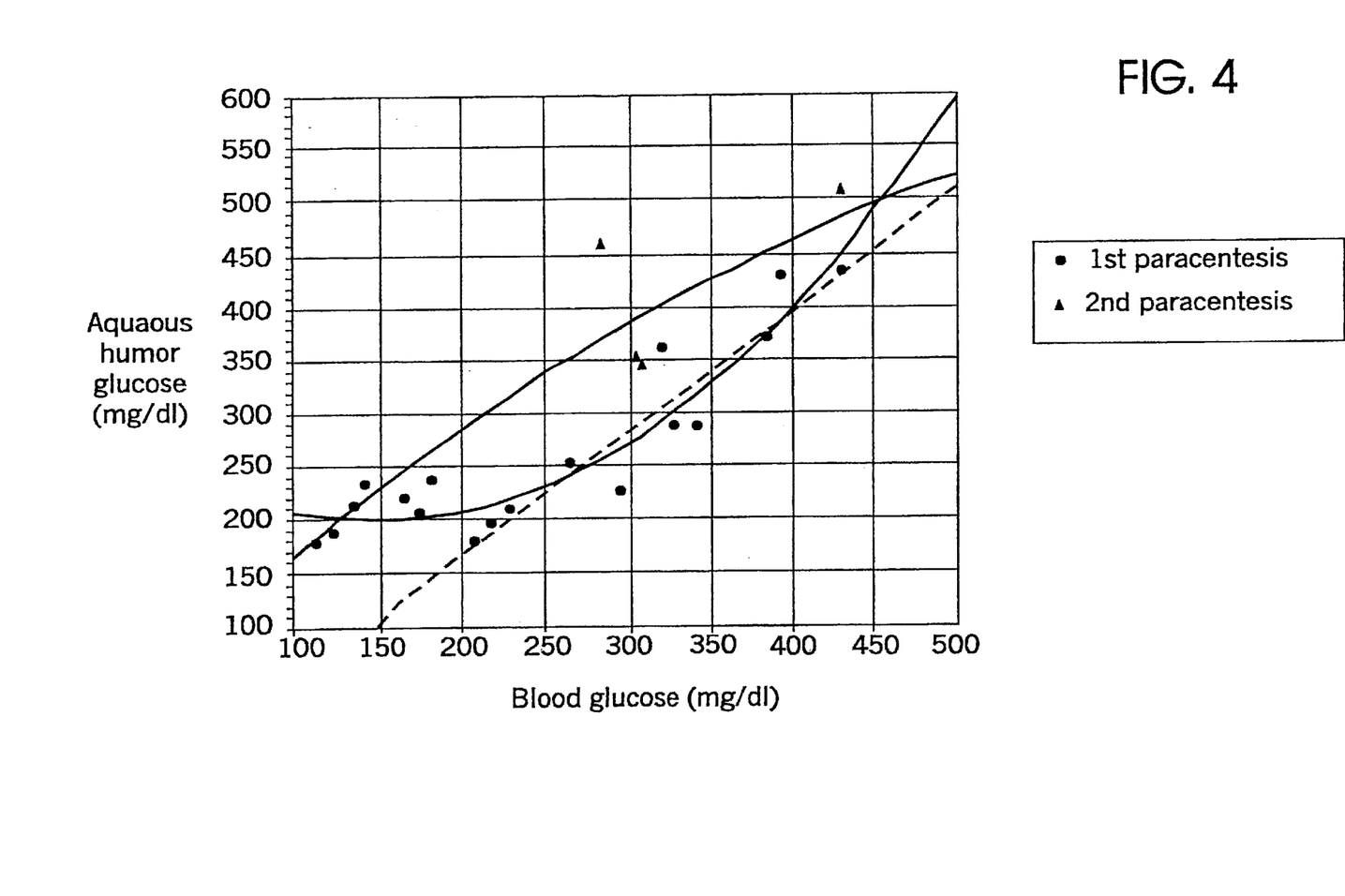
FIG. 4. Best-fit second-order polynomial curves demonstrate the relationship between aqueous humor glucose and plasma glucose while plasma glucose is rising in 9 animals. Aqueous glucose measurements from the first paracentesis of an eye correlate well with simultaneous plasma glucose (dark curve). When plasma glucose exceeds 200 mg/dL the relationship is nearly linear (dashed line). Aqueous humor glucose exceeds plasma glucose when plasma glucose is less than 200 mg/dL. The relationship of aqueous humor glucose with plasma glucose is different when the aqueous humor sample is obtained as a second paracentesis (light curve) suggesting that the initial paracentesis disrupts normal glucose homeostasis.

If only samples taken in the first fifteen minutes after anesthetic injection are considered, aqueous humor glucose concentration is higher than blood glucose concentration (207±28 mg/dL for aqueous humor; 135±27 mg/dL for blood). When calculated blood glucose rises above 200 mg/dL, simultaneous aqueous humor glucose parallels blood glucose nearly linearly [aqueous humor glucose=1.18 (blood glucose)−72.7; $r^2$=0.88]. (FIG. 4)

The number of aqueous humor samples from second paracenteses was insufficient to draw conclusions about their significance. They did not appear, however, to correlate well with aqueous humor glucose levels from initial paracenteses. (FIG. 4)

These data indicate that the baseline ratio of aqueous humor glucose to blood glucose in rabbits is approximately 1.5. (It may actually be higher than this as a true baseline was not obtained, and the blood glucose levels were likely elevated by the time the first samples were obtained, even in the first 15 minutes after injection.) This is much higher than in humans and higher than in previous reports on rabbits. All previous reports on rabbits, however, were prior to recognition of the hyperglycemic effect of xylazine anesthesia, yet many of them used xylazine anesthesia. In addition, most previous reports assumed that the rabbits were at steady-state euglycemia, without actually confirming that this was the case. These facts may account for some of the highly variable results in previous reports.

These data also demonstrate that aqueous humor glucose in the rabbit responds almost immediately once blood glucose exceeds 200 mg/dL. The relationship of aqueous humor glucose to blood glucose is nearly linear while blood glucose is rising above 200 mg/dL. Below that level, aqueous humor glucose appears stable. What happens to aqueous humor glucose when blood glucose is clamped at a hyperglycemic level, or when blood glucose concentration drops has yet to be determined. Nonetheless, equilibration of aqueous humor glucose with blood glucose probably occurs within minutes in rabbits. If rapid equilibration of aqueous humor glucose also occurs in humans, it could serve as an excellent substrate for non-invasive glucose monitoring.

Previous investigators have found no breakdown in the blood-aqueous barrier of albino rabbits exposed to infrared radiation with energy densities up to 106 J/cm (D. Reddy, supra; G. Peyman et al., *Exp. Eye Res.* 42, 249 (1986); T. Kurnik et al., *Inv. Ophthalmol. Vis. Sci.* 30, 717 (1989)). Infrared energy densities as low as 44 J/cm$^2$ may be sufficient to breakdown the blood-aqueous barrier in pigmented rabbits, however. This is still substantially higher than the energy density that would need be applied with the Raman technique disclosed herein.

EXAMPLE 5

Measurement of Integrity of Blood-Aqueous and Blood-Brain Barriers

The blood-brain and blood-aqueous barriers block passage of large molecules into the cerebrospinal fluid or aqueous humor. Many drugs and disease processes result in disruption of both the blood-aqueous barrier and the blood-brain barrier. In the case of such drugs or disease processes, disruption of the blood-brain barrier can be inferred from breakdown of the blood-aqueous barrier. Breakdown of the blood-aqueous barrier can be measured by measuring the protein content of the aqueous humor or by measuring the concentration of other substances (e.g., drugs) within the aqueous humor. Such substances may be quantifiable by Raman spectroscopy and the protein can be calculated from the fluorescence spectrum since the fluorescence spectrum is largely generated by protein. Consequently, the device disclose herein for measuring glucose and other Raman scattering metabolites in the eye can be used for measuring the integrity of the blood-aqueous and blood-brain barriers.

Raman scattering molecules of different sizes that do not normally cross the blood-aqueous or blood-brain barrier could be administered to a patient intravenously. The presence of these molecules is then quantified by Raman spectroscopy of the anterior chamber of the eye. This can be used to determine the size of molecules which pass through the blood aqueous barrier. The amount of fluorescence that is subtracted to reveal the Raman spectra of these substances, with the device disclosed herein would reflect the passage of natural proteins through the blood-aqueous and blood brain barriers.

Therapeutic drugs can also be measured to determine their effectiveness in crossing the blood-aqueous or blood-brain barrier.

The foregoing is illustrative of the present invention, and is not to be construed as limiting thereof. The invention is defined by the following claims, with equivalents of the claims to be included therein.

We claim:

1. A non-invasive method for determining blood glucose levels in a subject, comprising:

generating an excitation focusing said excitation laser beam into the anterior chamber of an eye of said subject so that aqueous humor in said anterior chamber is illuminated;

detecting a Raman spectrum from said illuminated aqueous humor;

subtracting a fluorescence spectrum for said aqueous humor from said Raman spectrum to produce a difference spectrum; and then determining the blood glucose level for said subject from said difference spectrum.

2. A method according to claim 1, wherein said laser beam has a duration not greater than thirty seconds.

3. A method according to claim 1, wherein said laser beam has an instantaneous power not greater than 30 milliwatts.

4. A method according to claim 1, wherein said focusing step is carried out so that energy on the retina of said eye from said excitation laser beam is not greater than 3000 milliwatts per square centimeter.

5. A method according to claim 1, further comprising the step of subtracting the spectrum of adjacent tissues from said Raman spectrum.

6. A method according to claim 1, wherein said subject is a human subject.

7. A method according to claim 1, wherein said determining step is carried out with an empirical model of actual testing experience.

8. A method according to claim 7, wherein said empirical model is generated by multivariate analysis.

9. A method according to claim 8, wherein said multivariate analysis is a partial least squares analysis.

10. A method according to claim 7, wherein:

said empirical model is produced with a training set comprising at least 20 aqueous humor samples, a Raman spectra corresponding to each of said samples, and a blood glucose level corresponding to each of said samples;

with the concentration of glucose in either the aqueous humor samples or corresponding blood samples varying by at least 200 mg/dL from the sample with the lowest concentration to the sample with the highest concentration.

11. A method according to claim 10, wherein the concentration of the principle Raman-active compounds in said samples vary substantially non-colinearly among said samples.

* * * * *

UNITED STATES PATENT AND TRADEMARK OFFICE
CERTIFICATE OF CORRECTION

PATENT NO. : 6,424,850 B1  Page 1 of 1
DATED : July 23, 2002
INVENTOR(S) : Lambert et al.

It is certified that error appears in the above-identified patent and that said Letters Patent is hereby corrected as shown below:

Title page,
Item [56], References Cited, OTHER PUBLICATIONS, the Wicksted reference should read as follows: -- Wicksted et al., Raman Spectroscopy Studies of Metabolic Concentrations in Aqueous Solutions and Aqueous Humor Specimens, *Applied Spectroscopy*, 49(7):987-993 (1995). --

Column 2,
Line 36, should read: -- U.S. Pat. No. 5,710,630 to Essenpreis suggests a method --

Column 6,
Line 37, should read: -- tration and the sample with the highest concentration. --

Column 12,
Line 40, should read: -- generating an excitation laser beam; --

Signed and Sealed this

Tenth Day of December, 2002

JAMES E. ROGAN
*Director of the United States Patent and Trademark Office*